United States Patent
Kumar et al.

(10) Patent No.: US 11,489,830 B2
(45) Date of Patent: Nov. 1, 2022

(54) SOURCE AUTHENTICATION OF WEBSITE CONTENT

(71) Applicant: KYNDRYL, INC., New York, NY (US)

(72) Inventors: Aman Kumar, Muzaffarpur (IN); Aarthi Arjunan, Bangalore (IN)

(73) Assignee: KYNDRYL, INC., New York, NY (US)

( * ) Notice: Subject to any disclaimer, the term of this patent is extended or adjusted under 35 U.S.C. 154(b) by 528 days.

(21) Appl. No.: 16/738,403

(22) Filed: Jan. 9, 2020

(65) Prior Publication Data
US 2021/0218736 A1    Jul. 15, 2021

(51) Int. Cl.
*H04L 29/06* (2006.01)
*H04L 9/40* (2022.01)
*G16B 10/00* (2019.01)
*G16B 50/40* (2019.01)

(52) U.S. Cl.
CPC .......... *H04L 63/0861* (2013.01); *G16B 10/00* (2019.02); *G16B 50/40* (2019.02)

(58) Field of Classification Search
CPC . H04L 63/0861; H04L 63/1483; G16B 10/00; G16B 50/40
See application file for complete search history.

(56) References Cited

U.S. PATENT DOCUMENTS

| | | | |
|---|---|---|---|
| 10,165,993 | B2 | 1/2019 | Kim et al. |
| 10,169,580 | B2 | 1/2019 | Hay et al. |
| 2017/0243028 | A1 | 8/2017 | LaFever et al. |
| 2017/0318008 | A1 | 11/2017 | Mead |

(Continued)

FOREIGN PATENT DOCUMENTS

| | | |
|---|---|---|
| DE | 102017113529 | 12/2018 |
| EP | 3417590 | 12/2018 |
| WO | 2018027300 | 2/2018 |

OTHER PUBLICATIONS

Gdad-s-river, "What Is Target Blank Anchor Tag Phishing Attack? How To Prevent It?", fossbytes.com, Feb. 16, 2017, 5 pages.

(Continued)

*Primary Examiner* — Brandon Hoffman
*Assistant Examiner* — William A Corum, Jr.
(74) *Attorney, Agent, or Firm* — John Kennel; Andrew M. Calderon; Calderon Safran & Cole P.C.

(57) ABSTRACT

Embodiments for authenticating a source of website content utilizing computer-generated or anonymized digital deoxyribonucleic acid (DNA) sequences include: receiving a request for a security sequence from a user device during a browser session; sending a first-generation digital DNA sequence (F1) to the device, wherein the F1 is generated from first and second DNA sequences (P1) and (P2) associated with a website; receiving a request for a second security sequence; generating a second-generation DNA sequence (F2) based on the F1 and the P1, wherein the F2 includes at least one genetic marker of the F1 and/or the P1; sending the F2 to the user device; receiving a request for security confirmation from the device; determining whether the F2 is a child DNA sequence of the F1 and/or the P1 utilizing Marker Assisted Selection techniques; and sending a response to the device indicating whether website content originates from the website.

20 Claims, 6 Drawing Sheets

(56) References Cited

U.S. PATENT DOCUMENTS

| | | |
|---|---|---|
| 2019/0020664 A1 | 1/2019 | Wood |
| 2019/0068638 A1 | 2/2019 | Bartik et al. |
| 2021/0099484 A1* | 4/2021 | Li .................... H04L 63/1483 |
| 2022/0070216 A1* | 3/2022 | Kohavi ............. H04L 63/1416 |

OTHER PUBLICATIONS

Anonymous, "Genetics and Inheritance", STEM-ED Scotland, University of Glasgow, accessed Sep. 23, 2019, 25 pages.

Kick, "EGNAS: an exhaustive DNA sequence design algorithm", BMC Bioinformatics, Jun. 20, 2012, 17 pages.

Anonymous, "Quantum Starts Here", IBM Quantum Computing, www.ibm.com/quantum.computing, accessed Sep. 23, 2019, 7 pages.

Alvarez-Rodriguez et al., "Quantum Artificial Life in an IBM Quantum Computer", Quantum Artificial Life in an IBM Quantum Computer, Scientific Reports 8, Article No. 14793, Oct. 4, 2018, 17 pages.

Anonymous, "Quantum key distribution", Wikipedia, accessed Sep. 23, 2019, 18 pages.

Garsiel et al., "How Browsers Work: Behind the scenes of modern web browsers", www.html5rocks.com, Aug. 5, 2011, 62 pages.

Mondal, "Marker Assisted Selection (MAS): Meaning, Steps and Application", www.biologydiscussion.com, accessed Oct. 7, 2019, 13 pages.

Anonymous, "An introduction to markers, quantitative trait loci (QTL) mapping and marker-assisted selection for crop improvement: The basic concepts", Springer Science + Business Media, Inc., Euphytica, vol. 142, Issue 1-2, Jan. 2005, 16 pages.

Mell et al., "The NIST Definition of Cloud Computing", NIST, Special Publication 800-145, Sep. 2011, 7 pages.

\* cited by examiner

SOURCE AUTHENTICATION OF WEBSITE CONTENT

BACKGROUND

Aspects of the present invention relate generally to online security and, more particularly, to utilizing computer-generated or anonymized digital deoxyribonucleic acid (DNA) sequences as a source indicator for authentication of website content to avoid phishing attacks.

Implementations of the present invention leverage general properties of computer-generated or anonymized digital DNA sequences to enable website source identification for the purpose of computer-based authentication, without the need to identify or understand any specific biological information (e.g., genetic instructions) that may be associated with such DNA sequences, and without the need to identify or understand the biological source of such DNA sequences.

Phishing is the fraudulent use of electronic communications to deceive or take advantage of users. One type of phishing attack takes advantage of situations where a user hits a link (anchor tag) on a web page, and it opens in a new browser tab.

SUMMARY

In a first aspect of the invention, there is a computer-implemented method for website authentication utilizing digital deoxyribonucleic acid (DNA) sequences as a source indicator during the website authentication, the method including: receiving, by a computing device, a request for a security sequence from a user device accessing a website during a browser session of the user device; sending, by the computing device, a first-generation deoxyribonucleic acid (DNA) sequence (F1) to the user device in response to the request, wherein the F1 is generated from a first DNA sequence (P1) and a second DNA sequence (P2) associated with the website; receiving, by the computing device, a request for a second security sequence from the user device accessing content of the website during the browser session; generating, by the computing device, a second-generation DNA sequence (F2) based on a cross of the F1 and the P1 in response to the request for the second security sequence, wherein the F2 includes at least one genetic marker of the F1 and/or the P1; sending, by the computing device, the F2 to the user device in response to the request for the second security sequence; receiving, by the computing device, a request for security confirmation from the user device, the request including the F2 and the F1; determining, by the computing device, whether the F2 is a child DNA sequence of the F1 and/or the P1 utilizing Marker Assisted Selection (MAS) techniques; and sending, by the computing device, a response to the request for security confirmation to the user device, wherein the response indicates whether the content originates from the website or originates from an outside source.

In another aspect of the invention, there is a computer program product for website authentication utilizing digital deoxyribonucleic acid (DNA) sequences as a source indicator during the website authentication, the computer program product including a computer readable storage medium having program instructions embodied therewith. The program instructions are executable by a computing device to cause the computing device to: send a request for a security sequence to a remote security server when the computing device is attempting to access a website during a browsing session; obtain, from the remote security server, a first-generation deoxyribonucleic acid (DNA) sequence (F1) in response to the request for the security sequence, wherein the F1 is based on a set of DNA sequences associated with the website; automatically request a second security sequence from the remote security server based on selecting content to access from the website; obtain a second-generation DNA sequence (F2) from the remote security server in response to the request for the second security sequence, wherein the F2 is based on the F1 and one of the set of DNA sequences associated with the website; automatically send a security confirmation request to the remote security server with the F1 and the F2 prior to accessing the content; determine whether the F2 originates from the F1 and/or the P1 based on a response to the security confirmation request from the remote security server; prevent display of the content when the F2 does not originate from the F1 and/or the P1; and enable display of the content when the F2 does originate from the F1.

In another aspect of the invention, there is system for website authentication utilizing digital deoxyribonucleic acid (DNA) sequences as a source indicator during the website authentication, the system including a processor, a computer readable memory, one or more computer readable storage media, and program instructions collectively stored on the one or more computer readable storage media for execution by the processor via the computer readable memory. The program instructions are executable to: receive a request for a security sequence from a user device accessing a website during a browsing session; send a first-generation deoxyribonucleic acid (DNA) sequence (F1) to the user device in response to the request, wherein the F1 is generated from a first DNA sequence (P1) and a second DNA sequence (P2) associated with the website; receive a request for a second security sequence from the user device accessing content of the website during the browsing session; generate a second-generation DNA sequence (F2) based on a cross of the F1 and the P1 in response to the request for the second security sequence, wherein the F2 includes at least one genetic marker of the F1 and/or the P1; send the F2 to the user device in response to the request for the second security sequence; receive a request for content authentication from the user device, the request including the F2 and the F1; determine whether the F2 is a child DNA sequence of the F1 and/or the P1 based on the at least one genetic marker of the F2 and at least one genetic marker of the F1 and/or the P1; and send a response to the request content authentication to the user device.

BRIEF DESCRIPTION OF THE DRAWINGS

Aspects of the present invention are described in the detailed description which follows, in reference to the noted plurality of drawings by way of non-limiting examples of exemplary embodiments of the present invention.

DETAILED DESCRIPTION

Aspects of the present invention relate generally to online security and, more particularly, to utilizing computer-generated or anonymized digital deoxyribonucleic acid (DNA) sequences as a source indicator for authentication of website content to avoid phishing attacks. According to aspects of the invention a system and method is provided for: generating unique parent DNA sequences to act as a source indicator for registered websites, providing first and second generation DNA sequences based on the unique parent DNA sequences to user devices accessing website content, and determining that DNA sequences provided by user devices originate from the unique parent DNA sequences assigned to a registered website, thereby authenticating the source of content to be accessed by the user device. Implementations of the present invention leverage general properties of DNA sequences to enable source identification for the purpose of computer-based authentication. In embodiments, DNA sequences are anonymized, resulting in DNA sequences that are not associated with the original source of the DNA (e.g., a particular plant from which a DNA sequence is derived). Methods of the invention may be implemented without the need to identify or understand any specific biological information (e.g., genetic instructions) that may be associated with such DNA sequences, and without the need to identify any original biological source (e.g., plant or animal) of the DNA sequence.

As noted above, phishing is the fraudulent use of electronic communications to deceive or take advantage of users. One type of phishing attack takes advantage of situations where a user hits a link (anchor tag) on a web page, and it opens in a new browser tab. In this situation, a bad actor (hacker) may take control of the original tab web page. In some instances, a bad actor can redirect the original tab's Uniform Resource Locator (URL) to a phishing page in the background that is designed to look like the real original page but asks for login credentials, in an attempt to access a user's confidential data. In such cases of cross site scripting, a bad actor may fool a user into believing that they are entering confidential data on a legitimate website, while they actually entered the data on an exact replica of the original website. In the case of a browser on a mobile phone, the URL disappears from view as a user scrolls down on a page, making it difficult for the user to notice that there is a phishing attack occurring. Implementations of the present invention provide a website content authentication service to users accessing website content in order to avoid problems associated with phishing attacks.

In implementations of the invention, a website is akin to a set of parents and all hyperlinks are akin to descendants of the parents. In implementations, a security server may provide secure browsing services to a number of remote clients. In aspects, website providers (clients) initially register to utilize the secure browsing service, and obtain a DNA stamp (parent DNA sequences) for their website, which is stored in a database of the security server. In implementations, every time a client's website is accessed by a user, the user's browser makes a call to the security server and receives a first-generation DNA sequence for the website (before the client's web page is displayed) which is generated based on the parent DNA sequences. When the user clicks a hyperlink of the web page or opens up a resource in a new tab, the user's browser again makes a call to the security server and receives a second-generation DNA sequence based on the parent DNA and first-generation DNA. In embodiments, a user device requests authentication of website content before opening the content, and the security server matches DNA sequences provided to the user with DNA sequences assigned to the parent to ensure that all the content is from a legitimate source. Only when the progeny DNA sequences match the parent DNA sequences will the user device display the content (e.g., web page). In implementations, the security server encrypts DNA sequences before sending them to a user device, thus avoiding potential DNA sequence theft.

Advantageously, embodiments of the invention provide a technical solution to the problem of insecure web browsing to ensure that no alien content is ever displayed on a web-browser of a user device. Aspects of the invention utilize the unique base-pairing characteristics of DNA sequences to determine parent/child relationships between security sequences, thereby providing a novel approach to online security. In implementations, security methods of the present invention may be utilized to track user traffic online (e.g., when two parties come together to exchange enough DNA information to determine where the traffic is originating from).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
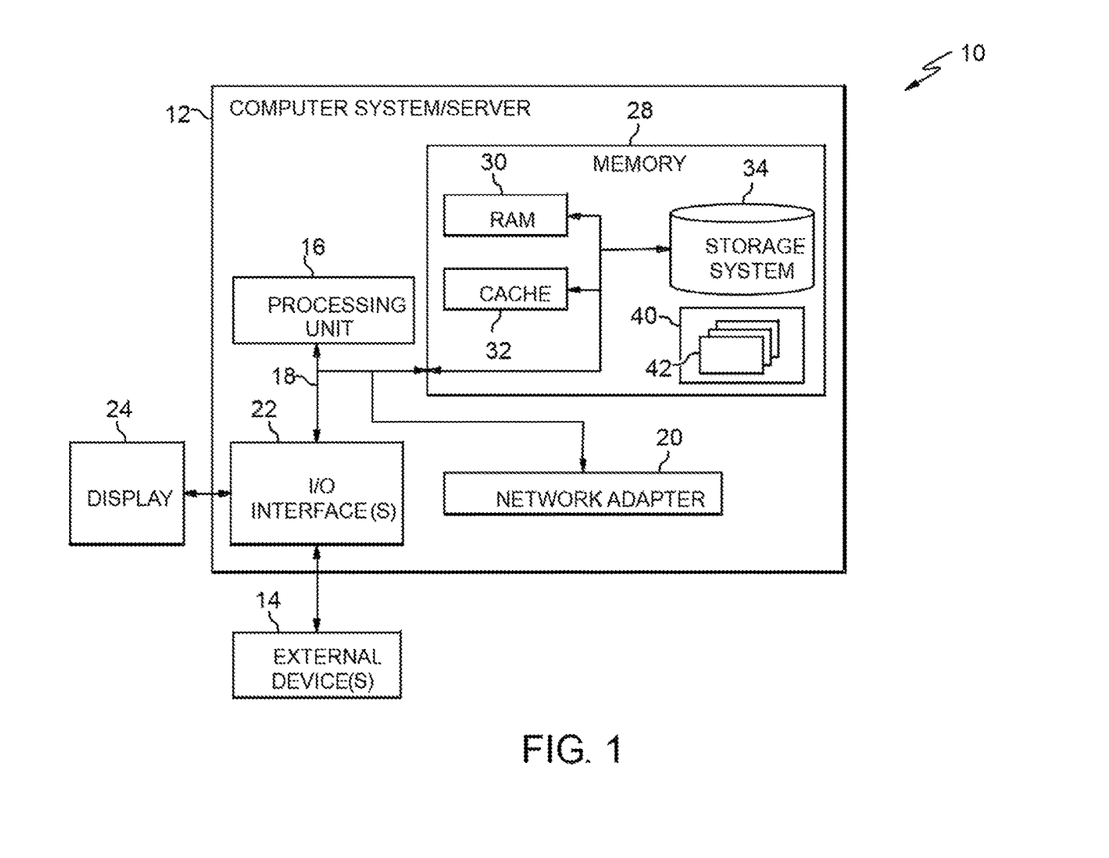
FIG. 1 depicts a cloud computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
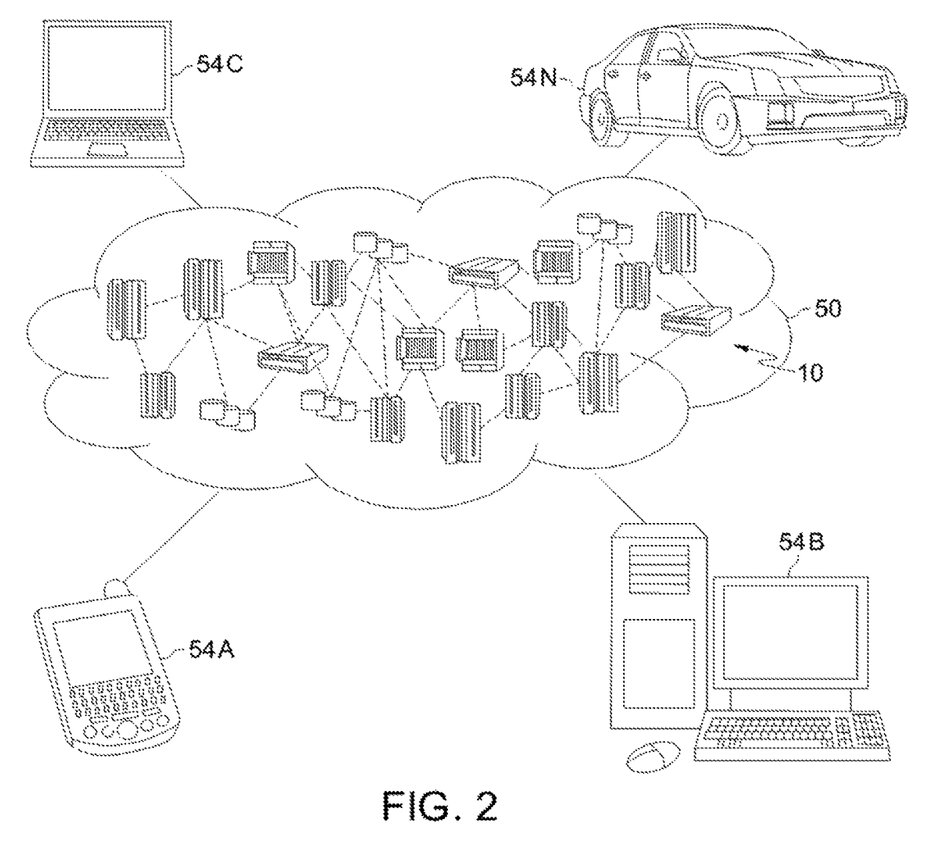
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
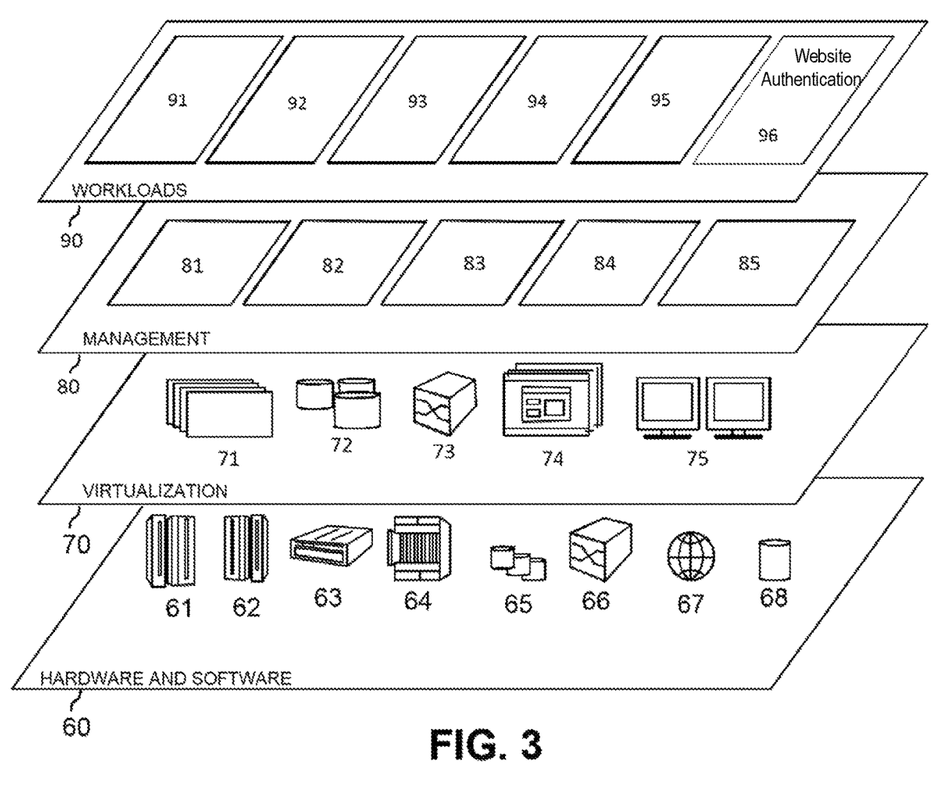
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61: RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks: virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and website authentication 96.

Implementations of the invention may include a computer system/server 12 of FIG. 1 in which one or more of the program modules 42 are configured to perform (or cause the computer system/server 12 to perform) one of more functions of the website authentication 96 of FIG. 3. For example, the one or more of the program modules 42 may be configured to: assign a set of parent DNA sequences to respective registered websites; generate and encrypt first-generation DNA sequences and second-generation DNA sequences in response to requests from remote user devices accessing content of the registered websites; and determine if content to be accessed by a user originates from the website or an outside source based on marker assisted selection techniques to determine that a second-generation DNA sequence originated from a first-generation DNA sequences associated with the website.

Figure 4:
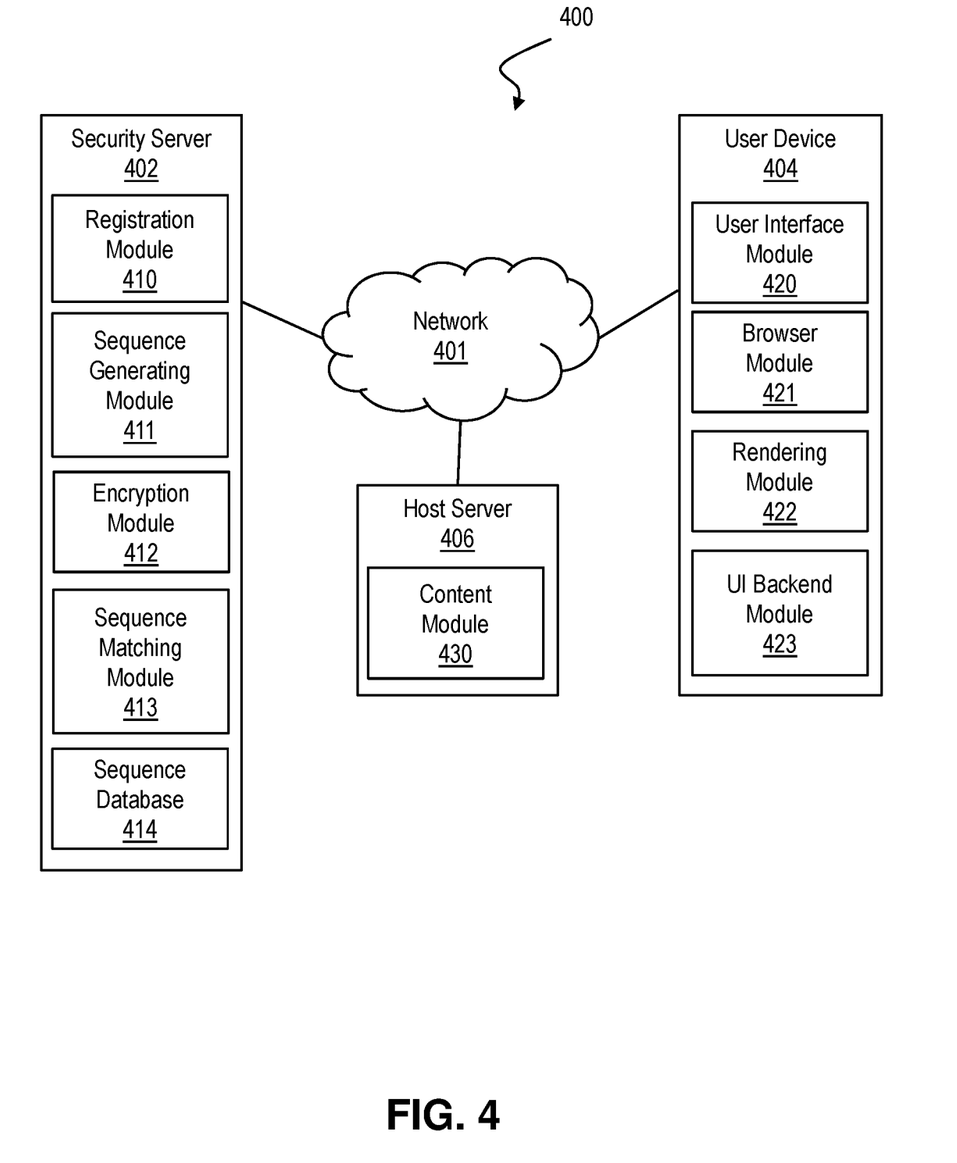
FIG. 4 shows a block diagram of an exemplary environment in accordance with aspects of the invention.

FIG. 4 shows a block diagram of an exemplary environment 400 in accordance with aspects of the invention. In embodiments, the environment 400 includes a network 401 connecting a security server 402 with a plurality of user devices represented at 404 and one or more host servers represented at 406. The user device 404 may include components of the computer system 12 of FIG. 1, and may be a desktop computer, laptop computer, tablet, smartphone, or other personal computing device. The host server 406 may also include components of the computer system 12 of FIG. 1, and may comprise a special purpose computing device configured to provide the user computer device 404 with access to a website and associated content.

The network 401 may be any suitable communication network or combination of networks, such as a local area network (LAN), a general wide area network (WAN), and/or a public network (e.g., the Internet). The security server 402 may be in the form of the computer device 12 of FIG. 1 and may be a special computing device configured to provide website authentication services to users accessing the content of websites registered with the security server 402.

Still referring to FIG. 4, the security server 402 may include one or more program modules (e.g., program module 42 of FIG. 1) executed by the security server and configured to perform one or more functions described herein. In embodiments, the security server 402 includes one or more of the following: a registration module 410, a sequence generating module 411, an encryption module 412, a sequence matching module 413 and a sequence database 414. In implementations, the registration module 410 is configured to register one or more websites of the host server 406, wherein the host server 406 may pay for the security server 402 to provide website authentication services to users accessing the website(s) of the host server 406.

In embodiments, the sequence generating module 411 is configured to generate and assign a set of parent DNA sequences to each registered website and store the DNA sequence data in the sequence database 414, and is also configured to generate first-generation DNA sequences and second-generation DNA sequences and send them to users accessing content of the host server 406 (e.g., via the user device 404). In embodiments, the encryption module 412 is configured to encrypt the first and second generation DNA sequences generated by the sequence generating module 411 before the first and second generation DNA sequences are sent to the users.

In aspects of the invention, the sequence matching module 413 receives DNA sequences from the user device 404 and matches the DNA sequences to stored DNA sequence information for the website to ensure that the second-generation DNA sequence originates from the first-generation DNA sequence and/or the parent DNA sequences. In embodiments, the sequence matching module 413 is also configured to send a response to a security confirmation request from the user device 404, wherein the response indicates whether content to be accessed by the user device 404 is authenticated (i.e., originates from the website and not an outside source).

With continued reference to FIG. 4, the user device 404 may include one or more program modules (e.g., program module 42 of FIG. 1) executed by the user device 404 and configured to perform one or more functions described herein. In embodiments, the user device 404 includes one or more of: a user interface module 420, a browser module 421, a rendering module 422 and a User Interface (UI) backend module 423. In implementations, the user interface module 420 is configured to enable a user to access content provided by the host server 406 (e.g., website content provided by a content module 430 of the host server 406); the browser module 421 is configured to enable website browsing by the user; the rendering module 422 is configured to enable or disable the display of content on a display (e.g., display 24 of FIG. 1) of the user device 404; and the UI backend module 423 is configured to receive first and second generation DNA sequences from the security server 402, decrypt encrypted content, send the first and second generation DNA sequences to the security server 402 with a request for authentication of website content prior to displaying the content, and determine whether to display the content based on a response to the request for authentication.

In embodiments, the security server 402 may include additional or fewer components than those shown in FIG. 4. In embodiments, separate components may be integrated into a single computing component or module. Additionally, or alternatively, a single component may be implemented as multiple computing components or modules. Additionally, the quantity of devices and/or networks in the environment 400 is not limited to what is shown in FIG. 4. In practice, the environment 400 may include additional devices and/or networks; fewer devices and/or networks; different devices and/or networks; or differently arranged devices and/or networks than illustrated in FIG. 4. Devices of the environment 400 may interconnect via wired connections, wireless connections, or a combination of wired and wireless connections.

Figure 5:
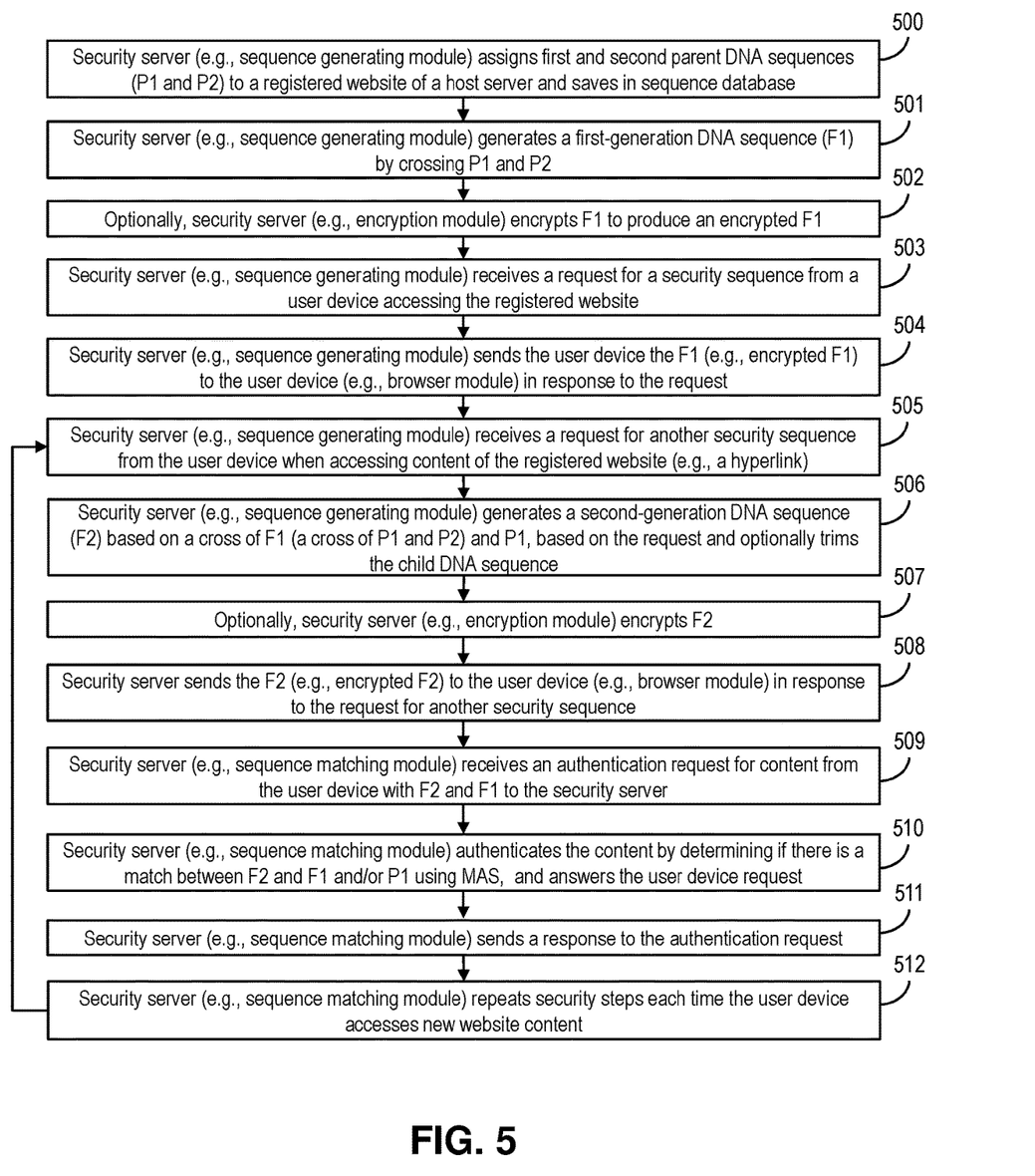
FIG. 5 shows a flowchart of an exemplary method in accordance with aspects of the invention implemented by a security server.

FIG. 5 shows a flowchart of an exemplary method in accordance with aspects of the present invention from the perspective of the security server 402. Steps of the method may be carried out in the environment of FIG. 4 and are described with reference to elements depicted in FIG. 4.

At step 500, the security server 402 assigns a set of parent deoxyribonucleic acid (DNA) sequences (a first parent DNA sequence P1 and a second parent DNA sequence P2) to a website of the host server 406 during registration of the website with the security server 402. The DNA sequences P1 and P2 comprise a series of characters based on DNA base pairing rules. In aspects, the security server 402 saves registration information for the website, including the P1 and the P2, in the sequence database 414. The sequence database 414 may securely store a plurality of digital DNA sequences and associated information for a number of clients (e.g., mapping sequence DNA to assigned websites) in order to provide website authentication services to users of the websites. Other registration data such as the identity of the website owner, services fees, etc., may also be saved in the sequence database 414. In implementations, the registration module 410 implements registration steps (e.g., collecting registration information, etc.), and the sequence generating module 411 performs the steps of generating the P1 and the P2 for a registered customer and saving the P1 and the P2 in the sequence database 414.

Molecular recognition based on the complementary base pairing of DNA is a fundamental principle utilized in the fields of genetics, DNA nanotechnology and DNA computing. This molecular recognition is based on the base pairing of complementary bases adenine (A)-thymine (T) and guanine (G)-cytosine (C). DNA sequence design algorithms have been developed to enable generation of DNA sequences with defined properties. One example of such an algorithm is the Exhaustive Generation of Nucleic Acid Sequence (EGNAS) tool for noncommercial use, which enables the input of user-defined options and criteria. In general, EGNAS utilizes a filter to select valid DNA sequences based on user-defined options and criteria, and generates possible digital DNA sequences of a desired length. Various tools may be used for generating the P1 and the P2. In one example, a DNA generating algorithm such as the EGNAS tool may be utilized, which enables the input of user-defined options and criteria. Electronic DNA sequence generating techniques may be utilized by the security server 402 in implementations of the invention, such that details of the DNA sequence generation need not be included herein. In implementations, the P1 and the P2 are actual DNA sequences (e.g., taken from plant DNA, one-celled organisms, bacteria, or insects). In embodiments, the DNA sequences are anonymized such that the sequences are removed from any identifying information regarding the original biological source of the DNA sequence. In other implementations, the P1 and the P2 are randomly generated DNA sequences.

Marker Assisted Selection or Marker Aided Selection (MAS) is an indirect selection process where a trait of interest is selected based on a genetic marker (morphological, biochemical or DNA/RNA variation) linked to the trait of interest (e.g., productivity, disease resistance, etc.), rather than on the trait itself. A genetic marker is a gene or DNA sequence with a known location on a chromosome that can be used to identify individuals or species. A genetic marker may be a short DNA sequence, such as a sequence surrounding a single base-pair change, or a long one. Breeding programs based on DNA markers to improve plant traits have been proposed. Instead of utilizing MAS techniques and genetic marker identification for physiological purposes, implementations of the invention utilize MAS techniques and genetic markers for the purpose of authenticating website content. That is, genetic markers are not utilized to identify individuals or characteristics of an organism, but are instead utilized for computer security protocols in accordance with embodiments of the invention.

In embodiments, the P1 and the P2 include genetic markers comprising a DNA sequence with a known location on a chromosome that can be used to identify individuals or species. For example, the genetic markers may be existing (actual) genetic plant markers. In aspects of the invention, the security server 402 enables clients to direct user devices (e.g., browser module 421 of the user device 404) to the security server 402 when they click on hyperlinks of the client's registered website. In embodiments, the security server 402 tags registered web pages with data (e.g. a DNA sequence generated by the security server 402) identifying the web pages as being registered with the security server 402.

At step 501, the security server 402 generates a first-generation digital DNA sequence (F1) by crossing the P1 and the P2 using DNA synthesis techniques to mirror the real-world transfer of DNA from parents (P1 and P2) to a child (F1). The term "cross" or "crossing" as used herein refers to combining portions of parent DNA sequences (e.g., P1 and P2) to produce a child DNA sequence (e.g., F1). In implementations, half of the F1 DNA is from the P1 and half the F1 DNA is from the P2. Optionally, the security server 402 shortens the F1 from an original length to an abbreviated length to limit computer resources needed to process and send the F1. Various methods of abbreviating the F1 may be utilized. In general, the length of the sequence should be long enough so that MAS techniques can be carried out for the sequence, but short enough so that the sequence does not become a computer processing burden (e.g. a burden on the browser module 421). For example, a browser module 421 fetching such a very long DNA sequence from the security server 402 would negatively impact user experience in terms of the amount of time it would take to display the website (web page).

In implementations, the F1 (original version or shortened version) includes one or more genetic markers inherited from the P1 and/or the P2. In one example, the F1 includes a first genetic marker from the P1 and a second genetic marker from the P2. Various tools for generating the F1 may be utilized in step 501, such as the EGNAS tool discussed above with respect to generating the P1 and the P2. In embodiments, the sequence generating module 411 implements step 501. The sequence generating module 411 may utilize a filter to select valid DNA sequences based on user-defined options and criteria, to generate possible sequences having certain characteristics (e.g., genetic markers).

Optionally, at step 502, the security server 402 encrypts the F1 to produce an encrypted F1. Various encryption techniques may be utilized in the performance of step 502. In embodiments, the encryption module 412 implements step 502.

At step 503, the security server 402 receives a request (call) for a security sequence from the user device 404 as a result of the user device 404 accessing a registered website. In implementations, data of the website or web page accessed by the user device 404 causes the browser module 421 of the user device 404 to call the security server 402. In embodiments, the sequence generating module 411 of the security server 402 receives the request for the security sequence from the user device 404.

At step 504, the security server 402 sends the user device 404 the F1 in response to the request received at step 503. In aspects, the F1 is generated as needed (e.g., in real-time or near real time) in response to the request received at step 503. In implementations, the security server 402 sends the user device 404 the F1 in encrypted form. In embodiments, the sequence generating module implements step 504.

At step 505, the security server 402 receives a request for another security sequence from the user device 404 when the user device 404 is accessing content of the registered website (e.g., clicks on a hyperlink) during a browser session. In implementations, data of the website or web page accessed by the user device 404 causes the browser module 421 of the user device 404 to call the security server 402 in accordance with step 505. In embodiments, the sequence generating module 411 of the security server 402 receives the request for the other security sequence from the user device 404 in accordance with step 505.

At step 506, the security server 402 generates a second-generation digital DNA sequence (F2) based on a cross of F1 (which is a cross of P1 and P2) and the P1 in response to the request received at step 505. In implementations, the F2 is a sequence of characters based on DNA base-pairs. In aspects, the F2 is generated as needed (e.g., in real-time or near real time) in response to the request. In implementations, half of the F2 DNA is from the F1 and half the F2 DNA is from the P1. Optionally, the security server 402 shortens the F2 from an original length to an abbreviated length to limit computer resources needed to process and send the F2. Various methods of abbreviating the F2 may be utilized. In implementations, the F2 (original version or shortened version) includes one or more genetic markers inherited from the F1 and/or the P1. In one example, the F2 includes a first genetic marker from the F1 and a second genetic marker from the P1 In embodiments, the sequence generating module 411 implements step 506.

At step 507, the security server 402 optionally encrypts the F2. Various encryption techniques may be utilized in the performance of step 502. In embodiments, the encryption module 412 implements step 507.

At step 508, the security server 402 sends the F2 to the user device 404 in response to the request received at step 505. In implementations, the F2 is sent in encrypted form according to step 507. In embodiments, the sequence generating module 411 implements step 508.

At step 509, the security server 402 receives an authentication request (web page or content authentication) from the user device 404 during a browser session, wherein the authentication request includes the F1 and the F2. In embodiments, the user device 404 automatically sends the authentication request to the security server 402 before the user device 404 opens or displays content from a registered website (e.g., after clicking a hyperlink of the website). In embodiments, the sequence generating module 411 implements step 509.

At step 510, the security server 402 authenticates that the content to be opened or displayed by the user device 404 does or does not originate from the registered website or web page. In implementations, the security server 402 determines if there is a match between the F2 and the F1 and/or the P1 using Marker Assisted Selection (MAS) techniques. As used herein, MAS refers to indirect selection for a desired phenotype based on the banding pattern of linked molecular (DNA) markers. MAS is based on the concept that it is possible to infer the presence of a gene from the presence of a genetic marker which is tightly linked to the gene of interest. MAS techniques may be utilized by the security server 402 to determine parent/child relationships between DNA sequences. In embodiments, the sequence matching module 413 implements step 510.

At step 511, the security server 402 sends a response to the authentication request received at step 509 to the user device 404. In implementations, the response includes an indication that the content to be opened by the browser module 421 does or does not originate from the main website. In aspects, the response includes a warning to a user (e.g., that the content is likely a phishing attack). In embodiments, the sequence matching module 413 implements step 511.

At step 512, the security server 402 repeats security steps 505-511 of FIG. 5 each time the user device 404 attempts to access new website content (e.g., each time the user of the user device 404 clicks on a hyperlink or opens a new tab) during the browser session. It should be understood that the security server 402 may thereby generate a number of unique progeny DNA sequences (e.g., F2, F3, F4, etc.) that are associated with the parent DNA (P1 and P2) of the original website accessed by a user. In this way, each progeny DNA sequence e.g., F2, F3, F4, etc.) can be compared to F1 and/or P by the security server 402 in accordance with step 510 to determine if the progeny DNA sequence is a child of F1 and/or P1.

Figure 6:
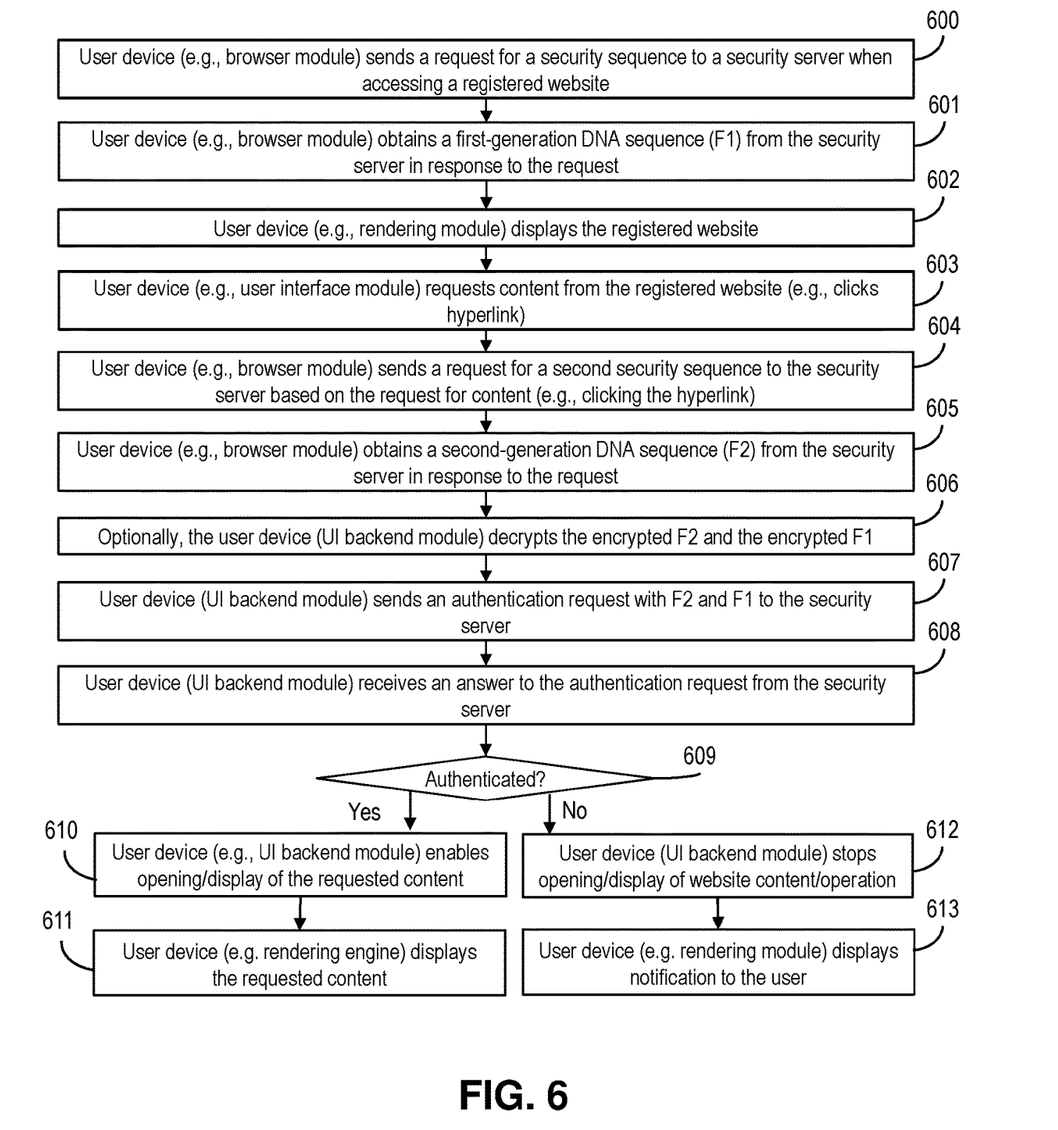
FIG. 6 shows a flowchart of an exemplary method in accordance with aspects of the invention implemented by a user device.

FIG. 6 shows a flowchart of an exemplary method in accordance with aspects of the present invention from the perspective of the user device 404. Steps of the method may be carried out in the environment of FIG. 4 and are described with reference to elements depicted in FIG. 4. Additionally, the steps of the method of FIG. 6 are intended to be implemented in conjunction with the steps of FIG. 5.

At step 600, the user device 404 sends a request for a security sequence to the security server 402 when attempting to access a website registered with the security server 402. In implementations, data provided by the website causes the user device 404 to automatically contact the security server 402 with the request during the browser session. In embodiments, the browser module 421 of the user device 404 implements step 600.

At step 601, the user device 404 obtains the F1 from the security server 402 in response to the request for the security sequence of step 600. As discussed above with respect to FIG. 5, the F1 is a first-generation DNA sequence generated by the security server 402 based on the set of parent DNA sequences P1 and P2 assigned to the website registered with the security server 402. In embodiments, the F1 is encrypted. In aspects, the user device 404 saves the F1 in a database of the user device 404. In implementations, the user device 404 does not open/display the website until it has obtained the F1 from the security server 402. In embodiments, the browser module 421 of the user device 404 implements step 600.

At step 602, the user device 404 displays the website of step 600. In implementations, the rendering module 422 displays the website on a display of the user device 404 upon receipt of the F1 from the security server 402, enabling a user to interact with content of the website.

At step 603, the user device 404 requests content from the registered website. In one example, a user selects a hyperlink of the website. In aspects, requesting content of the registered website causes the website to open a new tab that may be opened/displayed by the user device 404 after authentication of the new tab. In aspects, a user of the user device 404 utilizes the user interface module 420 of the user device 404 to implement step 603.

At step 604, the user device 404 automatically sends a request for a second security sequence to the security server 402 based on the request for the content (e.g., new tab to be opened). In aspects, the user device 404 automatically sends the request for the second security sequence based on data of the website. In embodiments, the browser module 421 of the user device 404 implements step 604.

At step 605, the user device 404 obtains (receives) the F2 from the security server 402 in response to the request of step 604. As noted above with respect to FIG. 5, the F2 is a second-generation DNA sequence generated by the security server 402 based on the F1 and the P1 DNA sequences associated with the registered website. In implementations, the F2 is encrypted. In embodiments, the browser module 421 of the user device 404 implements step 605.

Optionally, at step 606, the user device 404 decrypts the encrypted F1 and the encrypted F2. Various decryption methods may be utilized in the implementation of step 606. In embodiments, the UI backend module 423 of the user device 404 decrypts the F1 and the F2 in accordance with step 606.

At step 607, the user device 404 sends an authentication request to the security server 402, along with the F1 and the F2, during a browser session. In aspects, the user device 404 automatically sends the authentication request before opening/displaying the content based on UI code of the user device 404. In embodiments, the UI backend module 423 of the user device 404 automatically sends the authentication request with the F1 and the F2 to the security server 402 in accordance with step 607.

At step 608, the user device 404 receives an answer to the authentication request of step 607. In implementations, the answer includes information regarding whether the content to be accessed (of step 604) originates from the registered website or originates from another source (e.g., is a potential phishing attack). In aspects, the answer is in the form of a security warning. In implementations, the answer indicates that the F2 originates from the F1 and/or the P1. In embodiments, the UI backend module 423 of the user device 404 receives the answer in accordance with step 608.

At step 609, the user device 404 determines based on the answer of step 608 whether the content is authenticated (e.g., safe to open/display). In embodiments, the UI backend module 423 of the user device 404 implements step 609.

At step 610, the user device 404 enables opening/display of the content of step 603 based on a determination at step 609 that the content is authenticated (e.g., safe to open/display). In accordance with aspects of the invention, the user device 404 does not open or display the content of step 603 unless the content is authenticated at step 609. In embodiments, the UI backend module 423 of the user device 404 enables the browser module 421 to access the content in accordance with step 610.

At step 611, the user device 404 displays the requested content to the user. In implementations, the rendering module 422 renders the content for display on the user device 404.

Alternatively, at step 612, the user device 404 stops or prevents the opening/display of the requested content of step 603 based on a determination at step 609 that the content is not authenticated (e.g., likely originates from a bad actor or is a phishing attack). In embodiments, the UI backend module 423 of the user device 404 prevents the browser module 421 and the rendering module 422 from opening and displaying the requested content.

At step 613, the user device 404 optionally displays a notification to the user of the user device 404. In implementations, the UI backend module 423 of the user device 404 causes a warning to be displayed to the user indicating that the requested content likely originated from a source other than the registered website.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for website authentication utilizing digital deoxyribonucleic acid (DNA) sequences as a source indicator during the website authentication, the method comprising:
receiving, by a computing device, a request for a security sequence from a user device accessing a website during a browser session of the user device;
assigning, by the computing device, a first DNA sequence (P1) and a second DNA sequence (P2) to the website and saving the P1 and the P2 in a sequence database;
sending, by the computing device, a first-generation deoxyribonucleic acid (DNA) sequence (F1) to the user device in response to the request, wherein the F1 is generated from the P1 and the P2 assigned to the website;
receiving, by the computing device, a request for a second security sequence from the user device accessing content of the website during the browser session;
generating, by the computing device, a second-generation DNA sequence (F2) based on a cross of the F1 and the P1 in response to the request for the second security sequence, wherein the F2 includes at least one genetic marker of the F1 and/or the P1;
sending, by the computing device, the F2 to the user device in response to the request for the second security sequence;
receiving, by the computing device, a request for security confirmation from the user device, the request including the F2 and the F1;
determining, by the computing device, whether the F2 is a child DNA sequence of the F1 and/or the P1 utilizing Marker Assisted Selection (MAS) techniques; and
sending, by the computing device, a response to the request for security confirmation to the user device, wherein the response indicates whether the content originates from the website or originates from an outside source.

2. The computer-implemented method of claim 1, further comprising:
generating, by the computing device, the F1 based on the P1 and the P2, wherein the F1 includes at least one genetic marker of the P1 or the P2; and
storing, by the computing device, the F1 in the sequence database.

3. The computer-implemented method of claim 2, wherein the generating the F1 is provided by a service provider on a subscription, advertising, and/or fee basis.

4. The computer-implemented method of claim 1, further comprising encrypting, by the computing device, the F1 to produce an encrypted F1, wherein the sending the F1 to the user device comprises sending the encrypted F1 to the user device.

5. The computer-implemented method of claim 1, further comprising encrypting, by the computing device, the F2 to produce an encrypted F2, wherein the sending the F2 to the user device comprises sending the encrypted F2 to the user device.

6. The computer-implemented method of claim 1, wherein the P1 and the P2 comprise plant DNA, and the at least one genetic marker of the F1 is a genetic plant marker.

7. The computer-implemented method of claim 1, wherein the determining whether the F2 is a child DNA sequence of the F1 comprises matching at least one genetic marker of the F2 with the at least one genetic marker of the F1 and/or the P1.

8. The computer-implemented method of claim 1, wherein a service provider at least one of creates, maintains, deploys and supports the computing device.

9. The computer-implemented method of claim 1, wherein the computing device includes software provided as a service in a cloud environment.

10. A computer program product for website authentication utilizing digital deoxyribonucleic acid (DNA) sequences as a source indicator during the website authentication, the computer program product comprising a computer readable storage medium having program instructions embodied therewith, the program instructions executable by a computing device to cause the computing device to:
send a request for a security sequence to a remote security server when the computing device is attempting to access a website during a browsing session;
obtain, from the remote security server, a first-generation deoxyribonucleic acid (DNA) sequence (F1) in response to the request for the security sequence, wherein the F1 is generated based on a set of DNA sequences P1 and P2 assigned to the website by the remote security server;

automatically request a second security sequence from the remote security server based on selecting content to access from the website;

obtain a second-generation DNA sequence (F2) from the remote security server in response to the request for the second security sequence, wherein the F2 is based on the F1 and one of the set of DNA sequences P1 and P2 associated with the website;

automatically send a security confirmation request to the remote security server with the F1 and the F2 prior to accessing the content;

determine whether the F2 originates from the F1 and/or the DNA sequence P1 based on a response to the security confirmation request from the remote security server;

prevent display of the content when the F2 does not originate from the F1 and/or the DNA sequence P1; and enable display of the content when the F2 does originate from the F1.

11. The computer program product of claim 10, wherein the F1 is encrypted, and the program instructions further cause the computing device to decrypt the F1.

12. The computer program product of claim 11, wherein the F2 is encrypted, and the program instructions further cause the computer device to decrypt the F2.

13. The computer program product of claim 10, wherein the selecting content to access comprises clicking on a hyperlink of the website, and the program instructions further cause the computing device to send a notification to a user of the user device indicating that the content does not originate from the website when the computing device determines that the F2 does not originate from the F1 and/or the DNA sequence P1.

14. The computer program product of claim 10, wherein the set of DNA sequences comprise a set of existing DNA sequences including actual genetic markers.

15. A system for website authentication utilizing digital deoxyribonucleic acid (DNA) sequences as a source indicator during the website authentication, the system comprising:

a processor, a computer readable memory, one or more computer readable storage media, and program instructions collectively stored on the one or more computer readable storage media for execution by the processor via the computer readable memory, wherein the program instructions are executable to;

receive a request for a security sequence from a user device accessing a website during a browsing session;

assign a first DNA sequence (P1) and a second DNA sequence (P2) to the website and save the P1 and the P2 in a sequence database;

send a first-generation deoxyribonucleic acid (DNA) sequence (F1) to the user device in response to the request, wherein the F1 is generated from the P1 and the P2 assigned to the website;

receive a request for a second security sequence from the user device accessing content of the website during the browsing session;

generate a second-generation DNA sequence (F2) based on a cross of the F1 and the P1 in response to the request for the second security sequence, wherein the F2 includes at least one genetic marker of the F1 and/or the P1;

send the F2 to the user device in response to the request for the second security sequence;

receive a request for content authentication from the user device, the request including the F2 and the F1;

determine whether the F2 is a child DNA sequence of the F1 and/or the P1 based on the at least one genetic marker of the F2 and at least one genetic marker of the F1 and/or the P1; and send a response to the request content authentication to the user device.

16. The system of claim 15, wherein the program instructions are further executable to:

generate the F1 based on the P1 and the P2, wherein the F1 includes at least one genetic marker of the P1 or the P2; and store the F1 in the sequence database.

17. The system of claim 15, wherein the program instructions are further executable to encrypt the F1 to produce an encrypted F1, wherein the sending the F1 to the user device comprises sending the encrypted F1 to the user device.

18. The system of claim 15, wherein the program instructions are further executable to encrypt the F2 to produce an encrypted F2, wherein the sending the F2 to the user device comprises sending the encrypted F2 to the user device.

19. The system of claim 15, wherein the P1 and the P2 comprise existing DNA, and the at least one genetic marker is an actual genetic marker.

20. The system of claim 15, wherein the determining whether the F2 is a child DNA sequence of the F1 comprises utilizing Marker Assisted Selection (MAS) techniques to establish a parent and child relationship between the F2 and the F1.

* * * * *